US006273904B1

(12) United States Patent
Chen et al.

(10) Patent No.: US 6,273,904 B1
(45) Date of Patent: Aug. 14, 2001

(54) POLYMER BATTERY FOR INTERNAL LIGHT DEVICE (75) Inventors: James C. Chen, Bellevue; David J. Brown, Enumclaw; Brian D. Wilkerson; Charles M. McQuade, both of Issaquah; Darrin Huston, Enumclaw, all of WA (US)

(73) Assignee: Light Sciences Corporation, Issaquah, WA (US)

( * ) Notice: Subject to any disclaimer, the term of this patent is extended or adjusted under 35 U.S.C. 154(b) by 0 days.

(21) Appl. No.: 09/260,923

(22) Filed: Mar. 2, 1999

(51) Int. Cl.$^7$ ........................................................ A61N 5/06
(52) U.S. Cl. ................................. 607/88; 607/92; 606/14
(58) Field of Search ................................. 607/88, 89, 90, 607/92, 9, 33–37; 604/20; 606/2, 3, 7, 10–14

(56) References Cited

U.S. PATENT DOCUMENTS

| 3,794,041 | | 2/1974 | Frei et al. ............................ 128/348 |
| 5,047,044 | * | 9/1991 | Smith et al. .......................... 606/182 |
| 5,304,915 | * | 4/1994 | Sanpei et al. .......................... 320/14 |
| 5,411,537 | * | 5/1995 | Munshi et al. .......................... 607/33 |
| 5,616,140 | * | 4/1997 | Prescott .................................. 606/10 |
| 5,645,960 | * | 7/1997 | Scrosati et al. ....................... 429/219 |
| 5,702,432 | * | 12/1997 | Chen et al. ............................. 607/88 |
| 5,989,245 | * | 11/1999 | Prescott .................................. 606/14 |

OTHER PUBLICATIONS

Appetecchi, G.B.; and Scrosati, B. "Preliminary Note: A Lithium ion polymer battery." Electroclimica Acta. vol. 43 (9). 1998. pp. 1105–1107.
Bates, John.; and Dudney, Nancy J. "Thin Film Rechargeable Lithium Batteries for Implantable Devices." ASAIO Journal 1997; 43:M644–M647.

Gofer, Yosef; Sarker, Haripada; Killian, Jeffrey G.; Giaccai, Jennifer; Poehler, Theodore O., and Searson, Peter C. "Fabrication of an All–Polymer Battery on Derivatized Polythiophenes." Biomedical Instrumentation & Technology. Jan./Feb. 1998. pp. 33–38.
Teofilo, Vincent L.; and Nadell, Joel N. "Aerospace: Lithium Solid Polymer Batteries." IEEE AES Systems Magazines. May 1998. pp. 33–36.
Verdaasdonk, Rudolf M.; and Borst, Conrnelius. "Optics of Fibers and Fiber Probes." *Optical Thermal Response of Laser–Irradiated Tissue*. Plenum Press: New York, 1995. pp. 619–666.

* cited by examiner

Primary Examiner—Roy Gibson
(74) Attorney, Agent, or Firm—Ronald M. Anderson

(57) ABSTRACT

Several different embodiments of a flexible polymer battery are disclosed in connection with providing a medical therapy. For example, the electrical current from the polymer battery may be used to energize light sources for administering light therapy. In one embodiment, the polymer battery is formed as a substantially elongate structure having one end attached to an internal receiver coil, and the other end attached to a medical device such as a light probe that is adapted to be implanted within a patient's body. The polymer battery thus provides a conductive link between the internal receiver coil, which is electromagnetically coupled to an external transmitter coil for recharging the battery, and the light probe which is energized with current supplied by the flexible polymer battery. In another embodiment, the polymer battery is used to support a substrate on which a plurality of light sources are mounted in spaced-apart array. Yet other forms of the invention include polymer batteries within capsules or bead to energize light sources contained therein. The beads include receiver coils for recharging the polymer battery. Further, because of their small size, the beads or capsules are readily moved or held at a treatment site with an external magnet while therapy is rendered. Since a polymer battery includes very little metal, it is less likely to cause artifacts when the patient's body is imaged.

34 Claims, 5 Drawing Sheets

TO POWER
SOURCE

POLYMER BATTERY FOR INTERNAL LIGHT DEVICE

FIELD OF THE INVENTION

The present invention generally relates to an apparatus and a method for providing medical therapy at an internal treatment site within a patient's body, and more specifically, to an apparatus and a method for energizing a light source to provide the therapy at the internal treatment site, using a flexible polymer battery.

BACKGROUND OF THE INVENTION

In the 1970s, researchers discovered that polymer-salt complexes could serve as excellent electrolytes for solid state battery cells. In such a cell, the polymer is the electrolytic medium through which lithium cations are carried from a metallic lithium anode to a cathode composed of an intercalating material, such as titanium disulfide. The presence of a potential difference between the anode and the cathode of the polymeric cell produces an electric current through a load that is connected to the battery. There are several benefits associated with the use of a polymeric material as an electrolytic medium. Specifically, a polymer of this type is typically a non-volatile, non-corrosive, solid, and flexible material that may be easily processed into thin films and/or intricate shapes.

Almost since the discovery of polymer batteries, scientists have been conducting research into their possible uses. The minimal toxicity, lightweight, flexibility, and excellent energy storage capacity of polymer batteries has spurred development of their use in medical applications. One such application has been to provide electrical power to energize implanted pacemakers and defibrillators. There is much less concern about the toxicity of polymer batteries for such uses than more conventional Ni-Cd, or metallic hydride rechargeable batteries. Furthermore, polymer batteries can be fabricated with a minimal amount of metal, which avoids undesirable imaging artifacts that are often caused by implanted metal objects within a patient's body. Since polymer batteries are flexible, they can be distorted without damage, for example, to facilitate their insertion into a patient's body through a small incision.

Other medical applications for polymer battery power sources are likely to be developed. A prospective application of this technology that apparently has not yet been considered is providing power to energize implanted light sources to render light therapy. One type of light therapy, which is referred to as photodynamic therapy (PDT), is carried out after a photoreactive agent is administered to a patient. The photoreactive agent is preferentially absorbed by abnormal tissue at a treatment site, e.g., a tumor, rather than normal tissue. Light from a laser or other light source is administered to the treatment site to destroy the abnormal tissue. It is believed that the light absorbed by the sensitized abnormal cells that have absorbed the photoreactive agent produces singlet oxygen, which destroys the tumor cells.

Commonly assigned U.S. Pat. No. 5,445,608 discloses various embodiments for implanted probes that emit relatively low intensity light to administer PDT, and commonly assigned U.S. Pat. No. 5,800,478 discloses several embodiments for implantable flexible circuits on which light sources for administering PDT are mounted. The specification and drawings of both U.S. Pat. Nos. 5,445,608 and 5,800,478 are hereby specifically incorporated herein by reference. As disclosed in these two patents, the electrical current required to energize the LEDs or other light sources on the implanted probes can be provided from an external source coupled electromagnetically to an implanted receiver coil, or can be provided by a conventional storage battery that is implanted with the probe. Using a storage battery as a source of the electrical current energizing an implanted light probe or other medical device is preferable to providing the power at a fixed location to permit a patient to be mobile. Also, it may be preferable to employ a rechargeable battery if the PDT will likely continue for a very long period of time, to enable the therapy to continue without requiring further invasive procedures. However, conventional storage batteries represent a potential toxicity risk, are relatively heavy, and include metallic components that are undesirable when it is necessary to produce images of the patient's body using magnetic resonance imaging (MRI), or other imaging paradigms.

Accordingly, it would be desirable to energize light emitting sources (and other implanted medical devices) with polymer batteries to benefit from the lightweight, minimal metal content, and low risk of toxicity characteristics of such batteries. Moreover, polymer batteries can provide other functions and benefits not achievable with conventional batteries. For example, a flexible polymer battery can serve the purpose of a battery and its electrodes can serve as conductors extending between an implanted electromagnetic receiver and a medical device. A polymer battery can provide support for light sources or other electronic devices mounted in spaced-apart array on conductive traces applied to a flexible sheet. Further, a flexible polymer battery should provide heat sink capabilities, dissipating heat produced by light sources and other electronic devices. Because of the low toxicity of polymer batteries, they are ideal for inclusion in implanted capsules or beads designed to provide medical therapy, which may remain in a patient's body for an extended period of time.

SUMMARY OF THE INVENTION

In accord with the present invention, apparatus is defined for providing a medical therapy at a treatment site inside a patient's body. The apparatus includes a medical device that administers the medical therapy when energized by an electrical current. A polymer battery is coupled to the medical device to supply the electrical current. The polymer battery includes flexible electrodes and a polymer electrolyte that enables the polymer battery to be readily formed in at least one of three configurations. In a first configuration, the polymer battery is elongate and attached at one end to the medical device; in the second configuration, the polymer battery comprises a support for the medical device, serving as either a housing or a substrate. In different embodiments, the polymer battery is used either internally or externally of a patient's body. Finally, in the third configuration, the polymer battery and the medical device together comprise a bead or capsule. An envelope is provided for hermetically enclosing the polymer battery in the first configuration, and for hermetically enclosing both the polymer battery and the medical device in the second and third configurations. The envelope prevents fluids within the patient's body from interacting with the polymer battery.

Optionally, the apparatus may also include a current regulator and/or a voltage regulator to regulate either current or voltage supplied to the medical device. A switch may be included within the apparatus to control the electrical current flowing from the polymer battery to the medical device. The switch can be activated by either a pressure, a light signal, a radio signal, or a magnetic field.

The polymer battery is preferably adapted to connect to a source of a charging current disposed within the patient's body, so that the polymer battery can be recharged.

Electrical conductors are coupled between an anode of the polymer battery and the medical device and between a cathode of the polymer battery and the medical device. In a preferred application of this invention, the medical device comprises a light source for administering a light therapy to the treatment site.

In one embodiment, the envelope is substantially bead shaped and hermetically encloses both the polymer battery and the medical device, adapting them to be injected, ingested, or otherwise inserted into a patient's body. In another embodiment, the envelope is substantially capsule shaped, but also hermetically encloses both the polymer battery and the medical device, adapting the device for oral ingestion by a patient. In one embodiment, a receiver coil is enclosed within the envelope and is coupled to the polymer battery, enabling the polymer battery to be recharged when the receiver coil is exposed to a varying magnetic field. The varying magnetic field induces an electrical charging current to flow in the receiver coil to charge the polymer battery.

In yet another embodiment, the polymer battery is adapted to connect to a receiver coil implanted within the patient's body. This receiver coil is spaced apart from the medical device and is coupled thereto by the polymer battery. The polymer battery is charged with an electrical current from the implanted receiver coil. The charge current is induced to flow in the implanted receiver coil by a varying magnetic field supplied from outside the patient's body.

In still another configuration of the polymer battery, it comprises a substrate that supports a plurality of light sources arranged in a spaced-apart array. The substrate is sufficiently flexible to conform around or in a substantially non-planar treatment site within the patient's body, and in one embodiment is formed as a strip. The plurality of light sources are preferably coupled to an anode and a cathode disposed at opposite surfaces of the substrate.

Optionally, any of a low voltage sensor, an over current sensor, or a charge state indicator is provided. The low voltage sensor can interrupt current flow from the polymer battery to the medical device if a voltage of the polymer battery drops below a predefined level, while the over-current sensor can prevent damage to the battery during charging. The charge state indicator is useful for indicating a shelf charge state.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

Figure 1:
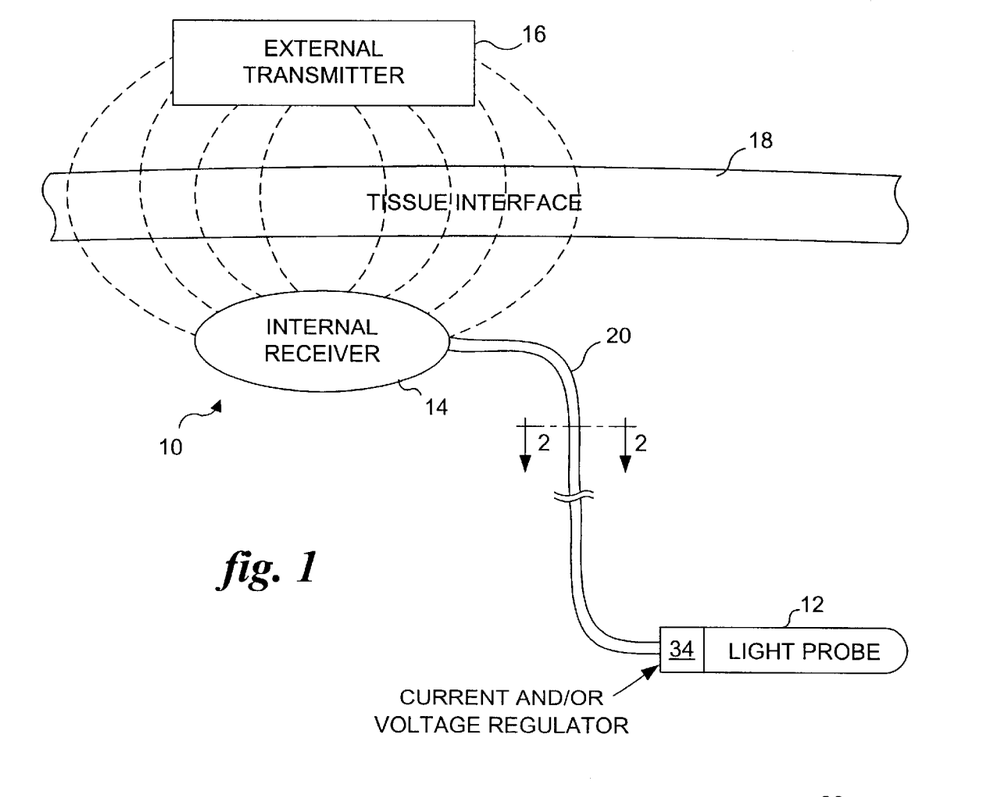
FIG. 1 is an exemplary view of apparatus for administering light therapy to a treatment site within a patient's body and including a polymer battery having an elongate shape, i.e., of a cord extending between an implanted electromagnetic receiver and a light probe.
Figure 2:
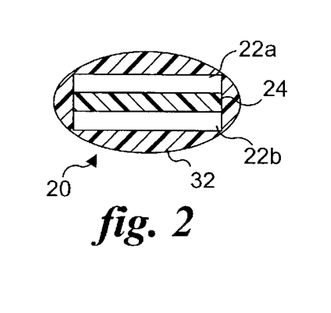
FIG. 2 is a cross-sectional view of the elongate-shaped polymer battery, taken along section line 2—2 in FIG. 1.
Figure 3:
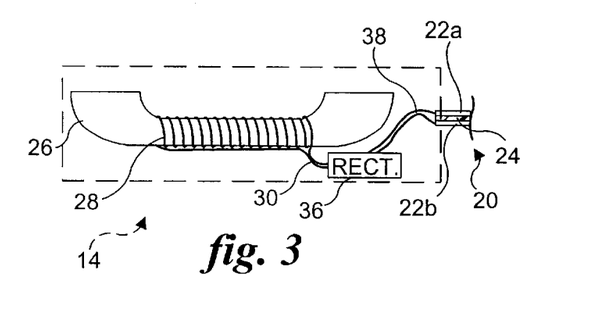
FIG. 3 is an elevational view of the transcutaneous receiver coil.

With reference to FIGS. 1–3, a first embodiment of the present invention is illustrated, along with a transdermal electromagnetic energy transfer system 10 that is used for providing energy to recharge an elongate flexible polymer battery 20. As shown therein, the flexible polymer battery is configured to have the shape of a cord that extends between an internal receiver 14 and a light probe 12. Details of internal receiver 14 are shown in FIG. 3. The internal receiver is electromagnetically coupled (as indicated by the dash lines) to an external transmitter 16. External transmitter 16 is adapted to be energized with alternating current (AC) provided by connection of the external transmitter to a controlled source that is coupled to the AC line (neither shown). External transmitter 16 produces a time varying magnetic field that electromagnetically couples to internal receiver 14. A varying magnetic field experienced by internal receiver 14 when the external transmitter is thus energized is coupled to a core 26, as shown in FIG. 3, causing a time varying or alternating current to be induced in a coil 28 that is wrapped around core 26. Core 26 preferably is fabricated from a metal or alloy having a characteristic relatively high magnetic permeability. While it is true that core 26 will likely cause artifacts during imaging of the patient's body, the internal receiver can be disposed some distance away from the treatment site that is being imaged. Thus, any imaging artifacts produced by the metallic material comprising core 26 should be minimized.

The AC signal induced in coil 28 is conveyed through leads 30 to a full wave rectifier 36, which converts the signal into a direct current (DC) signal. The DC signal developed by rectifier 36 is applied through leads 38 to one end of flexible polymer battery 20 to charge or recharge the battery.

FIG. 2 illustrates details of flexible polymer battery 20. It includes an upper electrode 22a and a lower electrode 22b that are spaced apart from each other and disposed on opposite sides of a flexible polymeric electrolyte 24. Various types of the electrodes and polymeric electrolytes can be used in constructing flexible polymer battery 20. For example, in one such battery, a TEFLON™ support for a carbon current collector is coupled to a poly-3,4,5-triflourophenyl biophene (3,4,5TFPT) anode. Preferably, the carbon current collector is a layer approximately 1–2 micrometers thick, and the 3,4,5TFPT anode is approximately 20 micrometers thick. Similarly, a TEFLON support for a carbon current collector is coupled to a poly-3,5-diflourophenyl thiophene (3,5DFPT) cathode. The thickness of the support, carbon collector, and cathode in the bottom electrode are approximately the same as that of the top electrode. In this example, polymeric electrolyte 24 is preferably a two-phase material comprising a gel with good ionic conductivity that is solution-cast into a thin, flexible film. Such a polymeric gel can be prepared by heating 3.7% by weight polyacrylonitrile (molecular weight=150,000) in 0.25% molar tetrabutylammonium tetrafluoroborate ($TBABF_4$) in propylene carbonate. The upper and lower electrodes and polymeric electrolyte extend the length of flexible polymer battery 20 and are enclosed within a biocompatible polymer sheath 32 that circumferentially seals the flexible polymer battery along its entire length, protecting it from exposure to bodily fluids.

As noted above, leads 38 couple respectively to the upper and lower electrodes at one end of flexible polymer battery 20, while a corresponding connection is made at the opposite end of the flexible polymer battery, to a current and/or voltage regulator 34 disposed at a proximal end of light probe 12. Current and/or voltage regulator 34 insures that the voltage and/or current supplied by flexible polymer battery 20 is regulated to levels appropriate to energize a plurality of light sources included in light probe 12. The light source in light probe 12 may comprise LEDs, fluorescent lights, electroluminescent devices, incandescent lights, arc lamps, and almost any other source of light energized with an electrical signal. Examples of light probes suitable for use in providing PDT when energized by flexible polymer battery 20 are disclosed in each of the commonly assigned above-referenced patents that have been incorporated herein by reference.

An advantage of flexible polymer battery 20 constructed as described above is that it does not include metal components, which as noted above, may cause artifacts when imaging a treatment site. In applications where such artifacts are of little or no concern, different configurations can be used for the flexible polymer battery. For example, the upper and lower electrodes can be formed from relatively thin metallic foil sheets that serve as positive and negative current collectors. A carbon anode that is only a few micrometers in thickness and is thus flexible is laminated on an upper flexible electrode sheet, while an equally thin manganese dioxide cathode is laminated to the flexible electrode sheet comprising the lower electrode. Between the upper and lower electrodes, a lithium ion polymer electrolyte layer is disposed.

A suitable gel-type electrolyte membrane for this polymer battery is prepared by dissolving lithium chlorate ($LiClO_4$) one molar solution in ethylene carbonate-diethyl carbonate (EC-DEC), in a 2:1 volume ratio mixture, stirring at 50° C. until complete dissolution occurs. Polyacrylonitrile (PAN) is then added, and the temperature is slowly increased to 100° C. to achieve gelification of the electrolyte. Dimensionally stable flexible polymer electrolyte layers are produced by casting the material between two glass sheets that are spaced apart by the desired thickness of the polymer electrolyte.

While the preceding discussion discloses two exemplary configurations for flexible polymer battery 20, it is not intended that the present invention in any way be limited to the specific details used for constructing a flexible polymer battery. It is contemplated that many other techniques and components may be employed for fabricating a flexible polymer battery useful in the present invention.

The physical configuration of flexible polymer battery 20 shown in FIG. 1 serves two distinct functions. Since one end of the battery is connected to implanted internal receiver 14 and the other end of the battery is connected to current and/or voltage regulator 34, the battery takes the place of a lead that might normally be used to couple the internal receiver to the light probe; in addition, the flexible polymer battery supplies energy to the load comprising the light probe. When electrical power stored in the polymer battery is exhausted, it is readily recharged with current supplied by the internal receiver, which is electromagnetically coupled to the external transmitter.

Flexible polymer battery 20 also serves as a tether that prevents the physical migration of light probe 12 away from its preferred disposition at the treatment site and facilitates the retrieval and removal of light probe 12 from the patient's body following completion of the light therapy administered by the probe. Furthermore, the pronounced extended elongate shape of the flexible polymer battery allows a relatively large battery mass to be inserted into the patient's body through a relatively small incision with minimal trauma. It should be evident that since the cross-sectional area (as shown in FIG. 2) of flexible polymer battery 20 is relatively small compared to its length, the battery and light probe can be inserted through a very small incision and advanced into the patient's body connected to light probe 12, so that the light probe is positioned as desired at the treatment site. Since the polymer battery is flexible and relatively lightweight, it does not substantially interfere with the positioning and maintenance of internal receiver 14 at its preferred disposition within a patient's body.

Figures 4A, 4B, 4C:
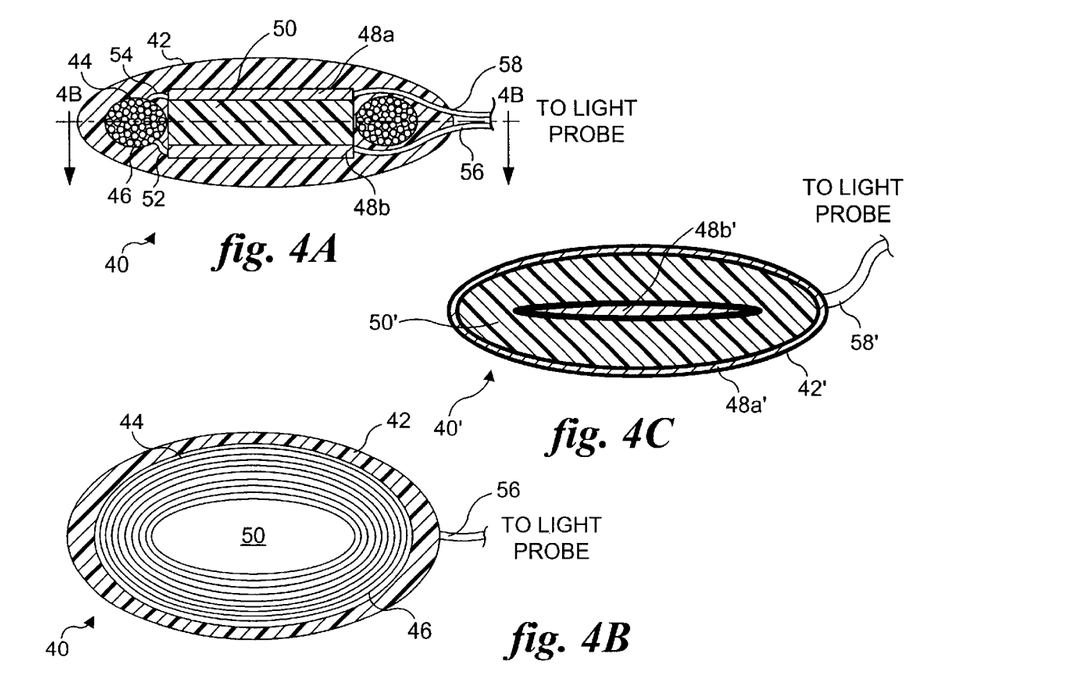
FIG. 4A is a sectional elevational view of another embodiment of an implantable electromagnetic receiver that includes a flexible polymer battery.
FIG. 4B is a cross-sectional view of the embodiment of the electromagnetic receiver of FIG. 4, taken along section line 4B—4B.
FIG. 4C is a cross-sectional view of an embodiment having a similar shaped to that of the embodiment shown in FIGS. 4A and 4B, but omitting the electromagnetic receiver.

FIGS. 4A and 4B illustrate another embodiment of the present invention 40 that combines an implantable receiver coil 44 with a flexible polymer battery that includes an upper electrode 48a and a lower electrode 48b. Sandwiched between the upper and lower electrodes is a flexible polymer electrolyte 50. The materials and procedure used to fabricate the flexible polymer battery are generally as described above in connection with flexible polymer battery 20. Not shown in FIG. 4A or 4B is a rectifier that is used for converting the alternating current induced in coil 44 from AC to DC for recharging the polymer battery. Current provided by the polymer battery is conveyed through leads 56 and 58 to the light probe or other implanted medical device that receives electrical energy from the flexible polymer battery. A biocompatible polymer 42 is used to encapsulate the concentric turns of a conductor 46 comprising the coil and the upper and lower electrodes and polymer electrolyte of the battery. While a conventional type of battery (e.g., a lithium-hydride battery) could be used to store energy in embodiment 40, the polymer battery is preferable, since it is relatively lightweight and minimizes the amount of metal implanted within the patient's body.

An embodiment of a polymer battery 40' having a shape very similar to that of the embodiment shown in FIGS. 4A and 4B is illustrated in FIG. 4C. However, unlike embodiment 40, the polymer battery in FIG. 4C does not include implantable receiver coil 44 and is not intended to be recharged by an external transmitter coil. Polymer battery 40' uses its internal volume for energy storage and has a substantially greater capacity than embodiment 40. A central electrode 48b' is generally surrounded by a polymer electrolyte 50', and an outer electrode 48a' surrounds the polymer electrolyte. A biocompatible polymer film 42' encapsulates outer electrode 48a' and protects the polymer battery from exposure to bodily fluids. A lead 58' includes conductors (not separately shown) that are connected to central electrode 48b' and outer electrode 48a', and the lead is hermetically sealed to the biocompatible polymer film. Embodiment 40' is thus capable of being implanted or otherwise disposed within a patient's body to supply electrical energy to a light probe or to another type of medical device. Once the charge on polymer battery is depleted, it can either be removed from the patient's body and replaced, if further power is required for the implanted light source or other medical device. Or, by connecting an appropriate power source to lead 58', the polymer battery can be recharged in place, or removed and recharged for reuse.

Figure 6:
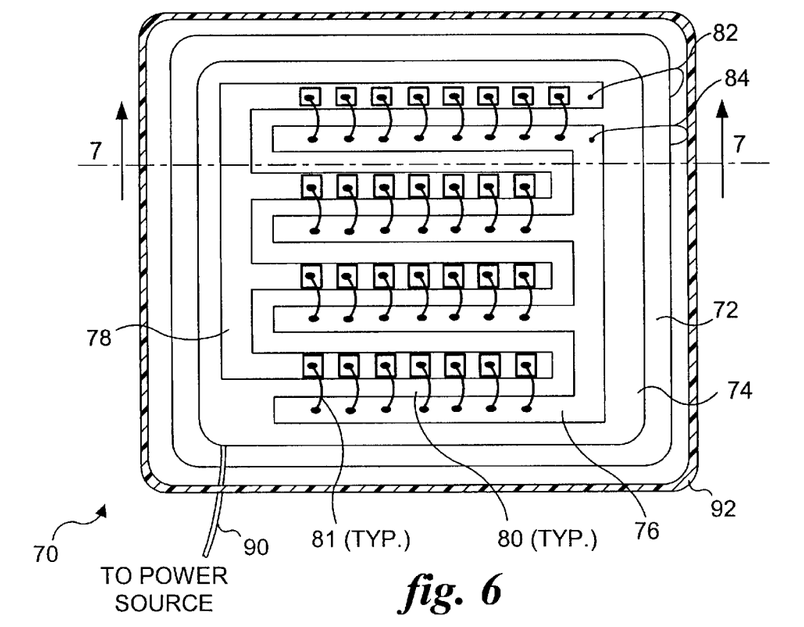
FIG. 6 is a planar view of a flexible panel with light sources, which includes a supporting flexible polymer battery.
Figure 7:
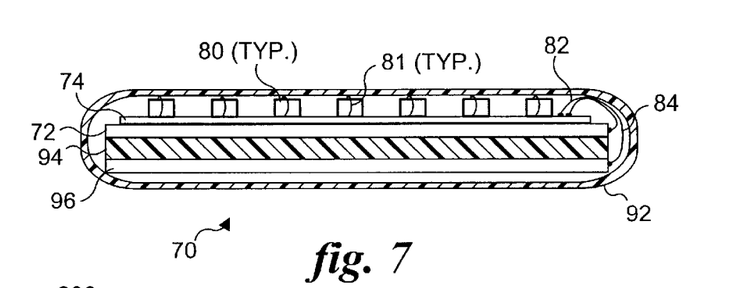
FIG. 7 is a cross-sectional view of the flexible panel from FIG. 6, taken along section line 7—7.

A flexible panel 70 that includes yet another embodiment of the present invention is illustrated in FIGS. 6 and 7. The flexible panel is shown with a substantially greater thickness than it actually would have. This panel includes a flexible substrate 74 disposed on a top electrode 72. A flexible conductive trace 76 is formed on the top surface of flexible substrate 74, in a pattern that includes a plurality of parallel strips that are coupled to each of a plurality of light sources 80 through conductors 81 that extend from the tops of the light sources to conductive traces 76. The other terminal (i.e., on the undersurface) of each of these light sources 80 is connected to a flexible conductive trace 78, which also comprises a plurality of parallel strips interdigitally interleaved between those of flexible conductive trace 76.

Flexible conductive traces 78 and 76 are connected respectively through leads 82 and 84 to top electrode 72 and a bottom electrode 96 of the polymer battery. A flexible polymeric electrolyte 94 is disposed between top electrode 72 and bottom electrode 96. The electrodes and the flexible polymer electrolyte are fabricated of the materials and using the procedures generally described above in connection with the other embodiments of the present invention. A lead 90 couples top electrode 72 and bottom electrode 96 to an internal receiver 14 like that shown in FIG. 1. When energized by electrical current from the polymer battery, light emitting sources 80 produce light of a desired waveband that is transmitted through an optically transparent, biocompatible polymer envelope 92. Envelope 92 is flexible and encloses the polymer battery and light sources, protecting them from contact with bodily fluids.

By forming the polymer battery as a flat, flexible, sheet-like structure, it serves well as a support for flexible substrate 74 and light sources 80. Further, the large surface area of top electrode 72 and bottom electrode 96 in the polymer battery help to dissipate heat generated by the light sources. The polymer battery panel 70 thus again implements multiple functions in this embodiment. Due to its flexibility, flexible panel 70 is more readily inserted into the patient's body and advanced to a desired treatment site, since it can readily be rolled and deformed as necessary while being maneuvered into place. In addition, it can be readily be flexed and molded to closely conform to a non-planar treatment site that is either convex or concave.

Figure 8:
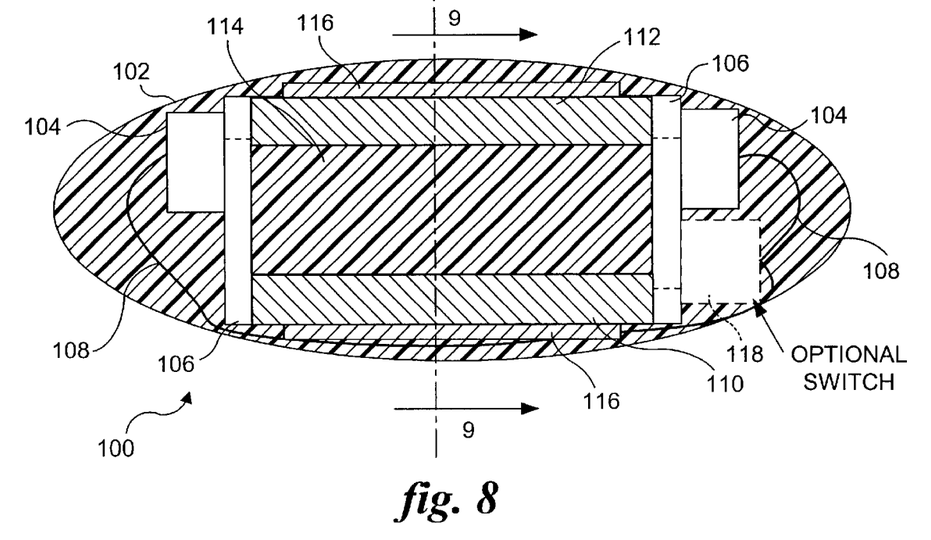
FIG. 8 is a sectional elevational view of a light therapy bead that includes a polymer battery.

Referring now to FIG. 8, a capsule 100 comprising yet another embodiment of the present invention is shown in a substantially enlarged illustration; the capsule is much smaller than shown and is intended to be sufficiently small to be inserted into a patient's body, e.g., through a needle, or orally administered. Alternatively, capsule 100 can be inserted into a patient's body through a small incision, or through another natural opening, for example, by ingestion, or as appropriate. However, capsule 100 is particularly applicable if orally ingested, since it can pass through the gastrointestinal tract, where it provides light therapy to the interior surface of the small intestine or colon. Once the light therapy is completed, the capsule is expelled along with other bodily waste.

Figures 11, 12, 14:
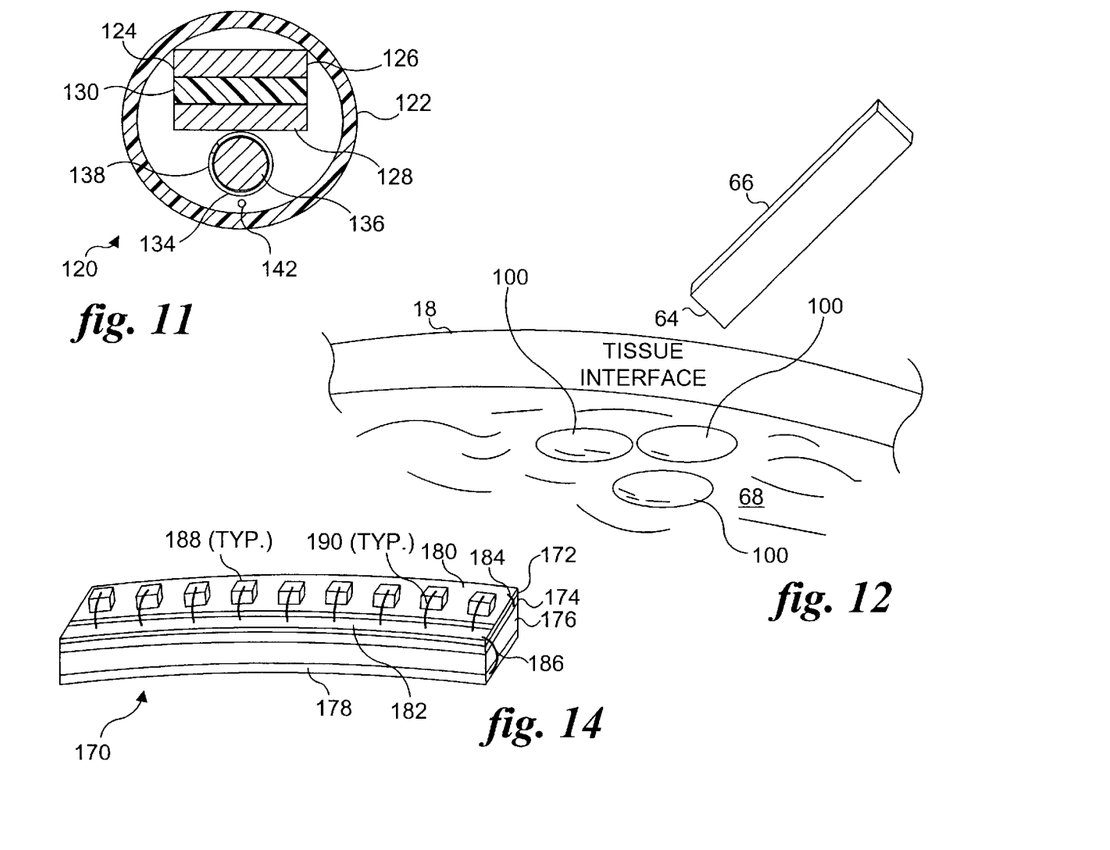
FIG. 11 is a cross-sectional view of the capsule of FIG. 10, taken along section line 11—11.
FIG. 12 is a schematic diagram of an internal treatment site showing how an external permanent magnet is used to attract implantable light sources such as the embodiments shown in FIGS. 8 and 9 (or in FIGS. 10 and 11)
FIG. 14 is another embodiment in which a flexible polymer battery is formed as a strip for supporting a plurality of light sources.

Referring back to FIG. 8, a ferrous (or ceramic magnetic) plate 116 is included within capsule 100 (optionally) to attract the capsule with an external magnet 66, generally as shown in FIG. 12. In this Figure, a plurality of capsules 100 are maintained at a desired treatment site 68 inside a patient's body using external magnet 66, by positioning a pole 64 of the external magnet immediately adjacent to a tissue interface 18. External magnet 66 is thus outside the patient's body, but the magnetic field it produces interacts with ferrous or ceramic magnetic plate 116 within each capsule 100 to hold the capsules at the treatment site during the duration of the treatment.

When treating esophageal or gastric cancer, it may be desirable to fix one or more capsules 100 at a desired treatment site within the gastrointestinal tract of the patient's body using external magnet 66. After the polymer batteries in the capsules become discharged, having supplied electrical current to produce the light administered to the treatment site, the external magnet is moved away from the patient's body, enabling the capsules to move through the gastrointestinal tract and be excreted. A plurality of capsules 100 can be swallowed, and/or individual capsules can be swallowed sequentially depending upon the total light fluence and the rate of fluence required. For other diseases, such as inflammatory bowel disease or intestinal polyposis, where the disease is less well localized, capsules 100 may be allowed to move via peristaltic contraction at their own rate, thereby illuminating a longer portion of the surface area within the gastrointestinal tract.

Figure 9:
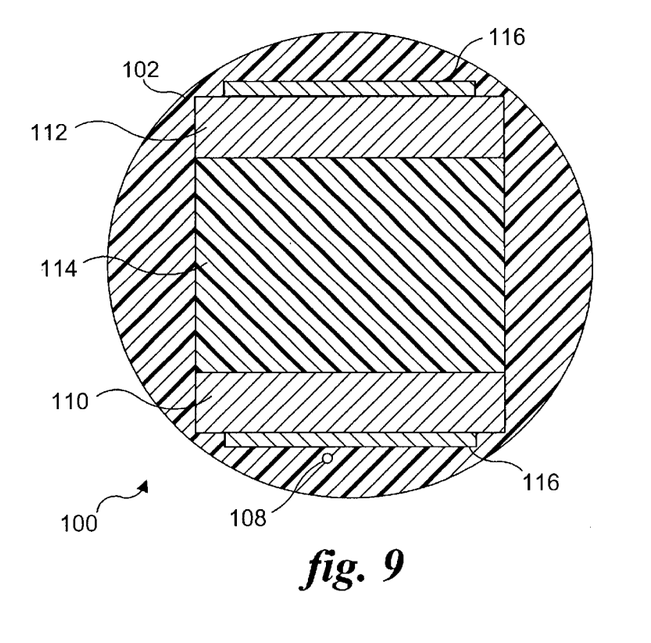
FIG. 9 is a cross-sectional view of the bead shown in FIG. 8, taken along section line 9—9.

Each capsule 100 is enclosed within a polymeric, optically transparent, biocompatible envelope 102 and includes one or more light sources 104. Each light source 104 is mounted on one of two parallel flexible substrates 106. Disposed between parallel flexible substrates 106, generally at the middle of capsule 100, is a polymer battery that includes a top electrode 112 and a bottom electrode 110. Disposed between the top and bottom electrodes is a polymer electrolyte 114.

One terminal of each of light sources 104, which are preferably LEDs in the preferred embodiment, passes through each flexible substrate 106 and is connected to top electrode 112. The other terminal of each of the light sources is connected to one side of an optional switch 118. When activated by a pressure signal, a light signal, a radio frequency (RF) signal, or a magnetic signal, optional switch 118 couples light sources 104 to lower electrode 110 of the polymer battery so that the light sources are energized with electrical current provided by the polymer battery. Since capsule 100 is self contained, it is not coupled to any other power source. Once the polymer battery is exhausted, no further light is emitted by light sources 104. Optional switch 118 thereby provides control means for determining when the light sources are energized so that optimal use is made of the light emitted by the light sources, for example, during PDT as the capsule passes through the gastrointestinal tract.

Optional switch 118 can also be employed with other of the embodiments disclosed herein, in applications where it is desirable to control the operation of the medical device that is provided current by the polymer battery.

Figure 5:
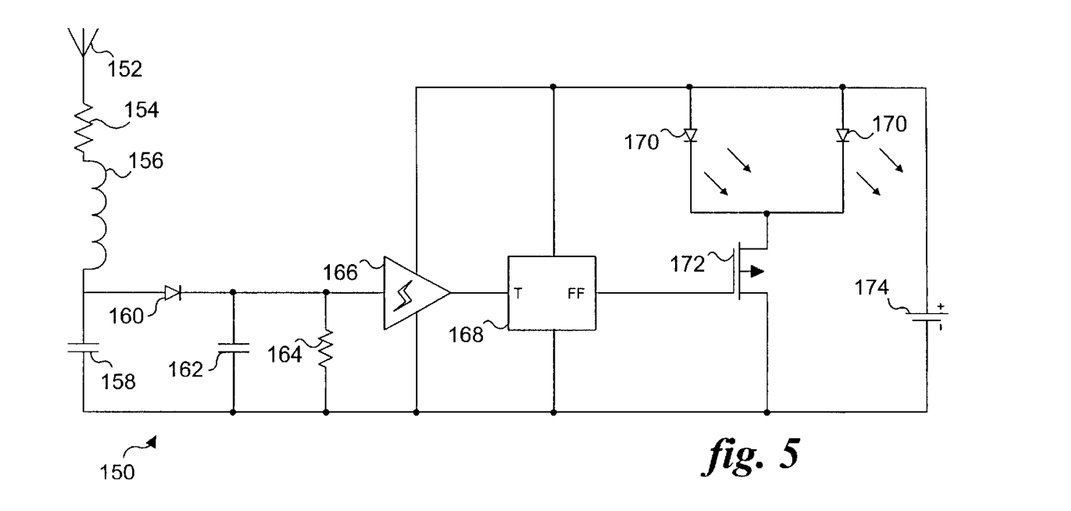
FIG. 5 is an electronic schematic diagram of a radio frequency pulsed switch for controlling the light sources in any of the implantable devices.

FIG. 5 illustrates an electrical circuit 150 that could be employed for optional switch 118. In this circuit, an antenna 152 is intended to receive an RF burst at a specific frequency. A resistor 154, an inductor 156, and a capacitor 158 comprise a tuned circuit having values selected to tune the circuit to the frequency of the RF burst. Diode 160 serves as a detector that provides an input signal to a filter comprising a capacitor 162 and a resistor 164. The signal on the cathode of diode 160 is filtered by capacitor 162 and resistor 164 and is input to a Schmidt trigger 166, which converts the RF burst to a digital pulse. The digital pulse is input to a flip-flop integrated circuit (IC) 168. The output of flip-flop IC 168 changes from low to high, or from high to low, each time that a pulse is received by circuit 150 and is applied to the gate of a MOSFET 172, enabling the MOSFET to conduct current supplied by a polymer battery 174 through LEDs 170 (or through other medical devices).

An external RF transmitter (not shown) having a directional antenna can be used to provide the RF burst. This RF signal should have sufficient strength when directed towards the portion of the patient's body in which capsule 100 is disposed to toggle MOSFET 172 into a conductive state, thereby enabling LEDs 170 to be energized. With the next RF burst that is transmitted from the external RF transmitter, the LEDs in capsules 100 can be toggled off.

It is also contemplated that instead of using an RF burst to control the application of electrical current to the light sources within capsule 100, a magnetic field such as that provided by external magnet 66, or a light pulse signal could be used to trigger an appropriate sensor. While electrical circuit 150 has been disclosed to show one embodiment of a circuit triggered with an RF burst, a Hall effect sensor responsive to an external magnetic field, or a photodiode responsive to light transmitted through the dermal layer could also be used to provide the control signal for activating the light sources or other medical devices contained within capsule 100.

Figure 10:
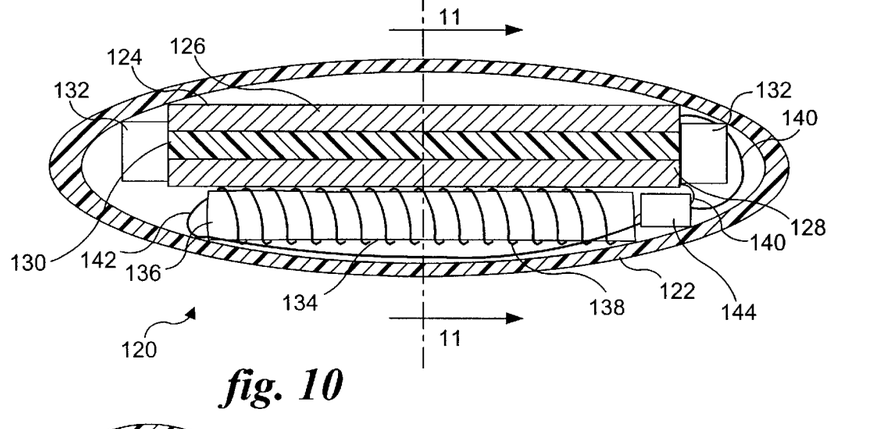
FIG. 10 is a sectional elevational view of another embodiment of a light therapy capsule that includes a receiving coil and a polymer battery.

A bead 120 comprising yet another embodiment of the present invention is illustrated in FIGS. 10 and 11. Bead 120 is protected by an optically transparent, flexible polymer envelope 122 that is biocompatible. The envelope completely encloses the bead, hermetically protecting the components from exposure to internal bodily fluids. Beads 120 are intended to be inserted into the body through an appropriate natural, incised, or puncture opening and then moved to a treatment site using external magnet 66, generally as shown in connection with capsules 100 in FIG. 12. Instead of including a ferro magnet or ceramic magnet that is attracted by the externally applied magnetic field, each of beads 120 includes a magnetic core 136 about which is coiled a plurality of turns of a conductor 138. Together, core 136 and conductor 138 comprise a receiver 134 for coupling to an externally produced electromagnetic field, generally like internal receiver 10, which is illustrated in FIG. 1.

As shown in FIG. 10, conductor 138 is coupled through a lead 142 to one side of a full wave rectifier 144; the other end of the conductor is connected to another input terminal of the full wave rectifier. The AC signal supplied by receiver 134 is converted to a DC signal by the full wave rectifier, and this DC signal is applied across an upper electrode 126 and a lower electrode 128 through leads 140. Light sources 132 include terminals at opposite sides that are coupled to top electrode 126 and bottom electrode 128 so that the light sources are energized by current from the flexible polymer battery. It is also contemplated that a remotely actuated switch can be used for controlling the flow of current to the light sources from the battery, like optional switch 118, which was discussed above in connection with capsules 100; however, the switch is not shown in FIG. 10. Each bead 120 includes its own internal receiver coil 134 and can be used to provide light therapy for a very prolonged period of time. A polymer battery 124 can be repeatedly recharged to provide light therapy or to energize a medical device.

For treating a diffuse volume in a patient's body, such as peritoneal carcinomatosis, beads 120 are mixed with a carrier fluid and injected with a hypodermic syringe (not shown) into the peritoneal cavity of the patient's body. External magnet 66 can be used to guide and move the beads to the treatment site for administration of the light therapy or other medical treatment administered with the beads. After the battery in each bead has been discharged, the external magnet may again be used to move the beads back to a more superficial site, for example, immediately under the skin of the abdominal cavity, so that the external magnetic field produced by the external transmitter can be electromagnetically coupled to receiver 134 in each bead for recharging polymer battery 124. Once the battery in each of the beads has been recharged, external magnet 66 is again used for repositioning the beads at the treatment site or at a different point within the treatment area for continuing the medical therapy.

Figure 13A:
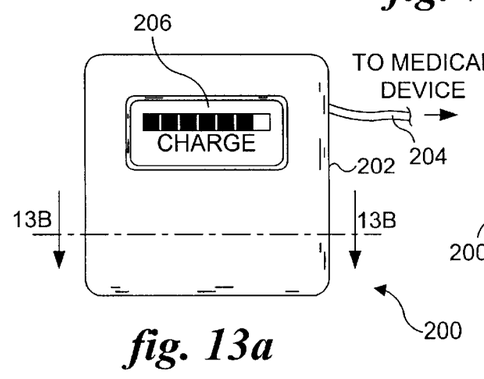
FIG. 13A is a plan view of an external battery supply in which the polymer battery comprises the housing.
Figure 13B:
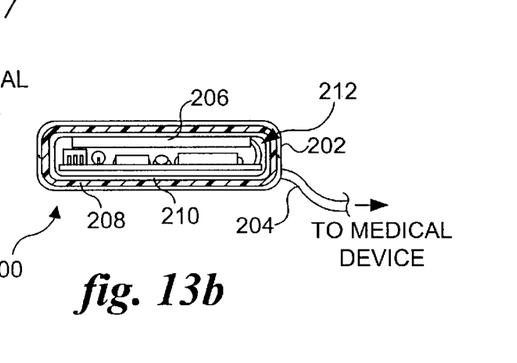
FIG. 13B is a cross-sectional view of the external battery supply shown in FIG. 13A.

FIGS. 13A and 13B illustrate an external polymer battery 200 in which the battery forms the housing for the device. An outer electrode 202 of the polymer battery is preferably coated with an insulating plastic layer or other material (not separately shown) to protect it. Outer electrode 202 preferably is split along a peripheral median line to provide access for electronic components 212 that are enclosed within the device. Within the outer electrode and in electrical contact with its inner surface is a polymer electrolyte layer 208. An inner electrode is in contact with the polymer electrolyte layer and forms the interior support for the housing of the device. A display 206 that indicates a charge state of the battery is provided on one surface of the housing and is formed of a liquid crystal display (LCD) panel or other suitable display. The charge state of the battery is at its max when the black bar extends fully across the display. Charge state is useful for indicating the shelf life remaining before the polymer battery is put into use, or for indicating the remaining charge while it is being used. However, display 206 can be used for displaying other types of information, such as the voltage level or current draw from the polymer battery. Electrical current provided by the polymer battery is supplied to a light probe or other medical device (implanted or otherwise—not shown) through a lead 204. It is contemplated that external polymer battery 200 might be provided with a belt clip or strap attached to its back surface to facilitate carrying it about while the electrical power it provides is employed to energize a medical device for rendering a medical treatment. By providing a compact power source of this type, the patient can readily remain ambulatory during the medical treatment.

With reference to FIG. 14, a flexible polymer battery 170 is shown, in which the battery is configured as a flexible strip. To simplify the drawing, a biocompatible polymer that envelopes the polymer battery and a plurality of light sources 188 mounted and supported thereby is not shown. Flexible polymer battery 170 includes a flexible insulating layer 172 on its top surface. An upper electrode 174 is disposed immediately below the flexible insulating layer, and under that are successively disposed a polymer electrolyte layer 176 and a bottom electrode 178. Extending along the top surface of flexible insulating layer 172 are two flexible conductive traces 180 and 182. Conductive trace 180 is electrically connected to top electrode 174 by a short conductor 184, while conductive trace 182 is electrically connected to bottom electrode 178 through a conductor 186. Light sources 188 are mounted on and in electrical contact with conductive trace 180. It should be noted that alternatively, a portion of flexible insulating layer 172 corresponding to the area of conductive trace 182 may be omitted, as well as conductive trace 180, so that light sources 188 are directly mounted on the upper surface of top electrode 176. Terminals of the light sources are connected to conductive trace 182 by conductors 190. Flexible polymer battery 170 can readily be inserted into a patient's body, e.g., through a small incision while rolled into a relatively compact configuration, and then endoscopically advanced to a treatment site and unfurled either around an outer surface or within a treatment site. For example, the flexible polymer battery can be wrapped around an outer convex surface of a tumor, or can be positioned within and conformed to a concave treatment site, for example, within an organ. The flexible nature of this embodiment of a polymer battery and its use as both a power source and a support for the light sources make it ideal for treatment of internal tumors or other sites that are non-planar.

Although the present invention has been described in connection with several preferred embodiments for practicing it, those of ordinary skill in the art will understand that many further modifications can be made thereto within the scope of the claims that follow. Accordingly, it is not intended that the scope of the invention in any way be limited by the above description, but instead be determined entirely by reference to the claims that follow.

What is claimed is:

1. Apparatus for providing a medical therapy at a treatment site inside a patient's body, comprising:
    (a) a medical device that administers the medical therapy when energized by an electrical current;
    (b) a polymer battery that is coupled to the medical device to supply the electrical current, the polymer battery having a polymer electrolyte that enables said polymer battery to be readily formed in at least one of three configurations, including:
        (i) a first configuration in which the polymer battery is elongate and integrally attached at one end to the medical device;
        (ii) a second configuration in which the polymer battery comprises one of a housing and a substrate for the medical device; and
        (iii) a third configuration in which the polymer battery and the medical device together comprise a capsule; and
    (c) an envelope for hermetically enclosing the polymer battery in the first configuration, and for hermetically enclosing both the polymer battery and the medical device in the second and third configurations, the envelope preventing fluids within the patient's body from contacting the polymer battery.

2. The apparatus of claim 1, further comprising a regulator that regulates one of a voltage and the electrical current supplied to the medical device.

3. The apparatus of claim 1, further comprising a switch that controls the electrical current flowing from the polymer battery to the medical device.

4. The apparatus of claim 3, wherein the switch is activated by one of a pressure, a radio signal, a light signal, and a magnetic field.

5. The apparatus of claim 1, wherein the polymer battery is adapted to connect to a source of a charging current disposed within the patient's body to charge the polymer battery.

6. The apparatus of claim 1, further comprising an electrical conductor coupled between an anode of the polymer battery and the medical device, and another electrical conductor coupled between a cathode of the polymer battery and the medical device.

7. The apparatus of claim 1, wherein the medical device comprises at least one of a plurality of light sources for administering a light therapy to the treatment site.

8. The apparatus of claim 7, further comprising a receiver coil that produces a charging electrical current when the receiver coil is exposed to a varying magnet field, said polymer battery being connected to the receiver coil to receive the charging electrical current, to charge the polymer battery.

9. The apparatus of claim 7, wherein the envelope is substantially bead shaped, said envelope being sized and shaped for injection into the patient's body.

10. The apparatus of claim 7, wherein the envelope is substantially capsule shaped, said envelope being adapted for oral ingestion by the patient.

11. The apparatus of claim 1, wherein the envelope is substantially bead shaped, the envelope hermetically enclosing both the polymer battery and the medical device and being adapted for injection into the patient's body.

12. The apparatus of claim 1, wherein the envelope is substantially capsule shaped, the envelope hermetically enclosing both the polymer battery and the medical device and being adapted for oral ingestion by the patient.

13. The apparatus of claim 1, further comprising a receiver coil enclosed within the envelope, said receiver coil being coupled to the polymer battery, enabling the polymer battery to be recharged when the receiver coil is exposed to a varying magnetic field, the varying magnetic field inducing an electrical charging current to flow in the receiver coil that charges the polymer battery.

14. The apparatus of claim 1, wherein the polymer battery is adapted to connect to a receiver coil implanted within the patient's body, said receiver coil being spaced apart from the medical device and coupled thereto by the polymer battery.

15. The apparatus of claim 14, wherein the polymer battery is charged by a charge current supplied by the implanted receiver coil, said charge current being induced in the implanted receiver coil by a varying magnetic field supplied from outside the patient's body.

16. The apparatus of claim 1, wherein the substrate of the second configuration of the polymer battery supports a plurality of light sources arranged in a spaced-apart array, said substrate being sufficiently flexible to conform around or within a substantially non-planar treatment site within the patient's body.

17. The apparatus of claim 16, wherein the plurality of light sources are coupled to an anode and a cathode disposed on the substrate.

18. The apparatus of claim 1, further comprising at least one of:
    (a) a low voltage sensor that interrupts current flow from the polymer battery to the medical device if a voltage of the polymer battery drops below a predefined level;
    (b) an over current sensor that is usable to detect an excess charging current applied to the polymer battery; and (c) a charge state indicator that provides an indication of a shelf charge state of the polymer battery.

19. Apparatus for providing a light therapy at a treatment site inside a patient's body, comprising:
  (a) a light source adapted for use inside a patient's body, the light source producing light to administer the light therapy when energized by an electrical current; and
  (b) a polymer battery adapted for use inside a patient's body having an elongate cable-like configuration with opposite ends, one end being connected to the light source to provide the electrical current for energizing the light source to administer the light therapy, and the other end being adapted to couple to a source of an electrical current for charging the polymer battery.

20. The apparatus of claim 19, further comprising means for hermetically enclosing the light source and the polymer battery, to provide protection from fluids within the patient's body.

21. For use within a patient's body, a method for supplying an electrical current to energize a medical device, comprising the steps of:
  (a) implanting a polymer battery inside the patient's body;
  (b) coupling said polymer battery electrically with the medical device, said polymer battery having a polymer electrolyte that enables said polymer battery to be readily formed in at least one of three configurations, including:
    (i) a first configuration in which the polymer battery is elongate and is integrally attached at one end to the medical device;
    (ii) a second configuration in which the polymer battery comprises one of a housing and a substrate for the medical device; and
    (iii) a third configuration in which the polymer battery and the medical device together comprise a capsule; and
  (c) supplying the electrical current to energize the medical device with the polymer battery.

22. The method of claim 21, further comprising the step of providing one or more hermetically sealed envelopes to protect the polymer battery and the medical device from contact with fluids within the patient's body.

23. The method of claim 22, further comprising the steps of providing an implanted recharging coil that is coupled to the polymer battery; and, energizing the implanted recharging coil with an electromagnetic field, producing a charging electrical current in the implanted recharging coil that charges the polymer battery.

24. A method for supplying an electrical current to energize a medical device implanted within a patient's body, comprising the steps of:
  (a) providing a polymer battery configured as a substrate having an upper surface, a lower surface, and sides;
  (b) supporting the medical device on the substrate comprising the polymer battery; and
  (c) electrically coupling the polymer battery to the medical device, so that electrical current flows from the polymer battery to the medical device to energize the medical device.

25. The method of claim 24, wherein the substrate comprises a sheet for supporting the medical device.

26. The method of claim 24, wherein the medical device comprises a plurality of light sources that are arranged in a spaced-apart array on the substrate, said light sources being used to administer a light therapy to a treatment site within the patient's body.

27. The method of claim 24, further comprising the step of hermetically enclosing the medical device and the polymer battery in a biocompatible envelope that is adapted to be ingested by a patient.

28. The method of claim 24, further comprising the step of hermetically enclosing the medical device and the polymer battery in a biocompatible envelope, forming a bead that is adapted for injection into the patient's body.

29. The method of claim 24, further comprising the steps of:
  (a) providing an electromagnetic receiver coil that is electrically coupled to the polymer battery to supply a charging current and is adapted to be energized with an externally applied electromagnetic field;
  (b) supplying the electromagnetic field to produce the charging current in the electromagnetic receiver coil;
  (c) recharging the polymer battery with the charging current after the polymer battery has become at least partially discharged.

30. The method of claim 24, further comprising the step of regulating at least one of a voltage and a current supplied to energize the medical device.

31. The method of claim 24, further comprising the steps of:
  (a) sensing a voltage of the polymer battery; and
  (b) interrupting the electrical current supplied to the medical device from the polymer battery if the voltage of the polymer battery decreases below a predefined level.

32. Apparatus for delivering a medical treatment to a patient, comprising:
  (a) a medical device that is adapted to deliver the medical treatment to the patient; and
  (b) a housing for the medical device, said housing being disposed around at least a portion of the medical device, said housing comprising a polymer battery that includes a polymer electrolyte and a plurality of electrodes that are electrically connected to the medical device, said polymer battery supplying an electrical current to energize the medical device.

33. Apparatus for delivering an electrical current to energize a medical device used by an ambulatory patient, comprising:
  (a) a housing, said housing being formed of a polymer battery that includes an outer electrode, an inner electrode, and a polymer electrolyte disposed between the outer electrode and the inner electrode, said outer electrode defining a substantial portion of a shape of the housing; and
  (b) a lead having a connection with the polymer battery, said lead conveying electrical current supplied thereby to the medical device.

34. The apparatus of claim 33, further comprising a display mounted in the housing, said display indicating one of a condition of the polymer battery and a parameter related to the electrical current supplied to the medical device.

* * * * *